(12) United States Patent
Swope et al.

(10) Patent No.: US 7,878,994 B2
(45) Date of Patent: Feb. 1, 2011

(54) CAST FOR IMMOBILIZING AND HEATING OR COOLING A BODY PART

(76) Inventors: Joseph Michael Swope, 13017 Wisteria Dr., #343, Germantown, MD (US) 20874; Heather Anne Swope, 13017 Wisteria Dr., #343, Germantown, MD (US) 20874

( * ) Notice: Subject to any disclaimer, the term of this patent is extended or adjusted under 35 U.S.C. 154(b) by 965 days.

(21) Appl. No.: 11/699,128

(22) Filed: Jan. 29, 2007

(65) Prior Publication Data

US 2008/0183117 A1    Jul. 31, 2008

(51) Int. Cl.
*A61F 5/00* (2006.01)
*A61F 5/37* (2006.01)

(52) U.S. Cl. ............. 602/14; 602/2; 602/3; 602/5; 602/6; 602/12; 602/20; 602/21; 602/22; 128/880

(58) Field of Classification Search ........... 602/2–3, 602/5, 8–9, 60–66; 128/873–875, 869–870, 128/882
See application file for complete search history.

(56) References Cited

U.S. PATENT DOCUMENTS

| | | | |
|---|---|---|---|
| 3,463,161 A * | 8/1969 | Andrassy | 607/110 |
| 4,061,897 A * | 12/1977 | Thykeson | 219/211 |
| 4,445,507 A | 5/1984 | Eisenberg | |
| 4,565,195 A | 1/1986 | Eisenberg | |
| 4,653,490 A | 3/1987 | Eisenberg | |
| 4,753,241 A * | 6/1988 | Brannigan et al. | 607/112 |
| 5,027,801 A | 7/1991 | Grim | |
| 5,058,576 A | 10/1991 | Grim | |
| RE35,113 E | 12/1995 | Grim | |
| 6,000,402 A * | 12/1999 | Able | 128/869 |
| 6,005,041 A | 12/1999 | Cook | |
| 6,324,703 B1 | 12/2001 | Chen | |
| 6,676,619 B2 * | 1/2004 | Arden | 602/8 |
| 6,840,955 B2 | 1/2005 | Ein | |
| 7,022,093 B2 * | 4/2006 | Smith et al. | 602/2 |
| 7,055,575 B2 * | 6/2006 | Noel | 165/10 |
| 7,094,212 B2 * | 8/2006 | Karason et al. | 602/5 |

* cited by examiner

*Primary Examiner*—Patricia M Bianco
*Assistant Examiner*—Brandon Jackson
(74) *Attorney, Agent, or Firm*—Donald A. Kettlestrings

(57) ABSTRACT

A flexible cast that constructed out of a group of cells. Each cell is filled with a filler that contains a substance that can be heated or cooled. The cast is held onto the user's body by a set of straps and fasteners. The cast is intended to immobilize the body part and either heat or cool it as desired.

13 Claims, 2 Drawing Sheets

CAST FOR IMMOBILIZING AND HEATING OR COOLING A BODY PART

CROSS-REFERENCE TO RELATED APPLICATIONS

No

FEDERALLY SPONSORED RESEARCH

No

SEQUENCE LISTING OR PROGRAM

No

FIELD OF INVENTION

This invention relates to casts. More specifically it relates to casts that can heat or cool a body part. Even more specifically it relates to flexible casts that can heat or cool a body part.

BACKGROUND OF THE INVENTION

Both casts and therapeutic heating and cooling pads are well known to the art, but none have been combined in with the elements of this invention.

A large number of cast designs have been invented and patented in the United States. Examples are U.S. Pat. Nos. 4,653,490, 4,565,195 and 4,445,507, all by Eisenberg; U.S. Pat. No. 6,676,619 by Arden; and U.S. Pat. No. 5,058,576 by Grim. Eisenberg describes a series of thumb immobilizers that prevent movement of the thumb. Some of the Eisemberg designs use a system of straps to hold the brace in place, while others use a glove. The Eisenberg inventions seem to be limited to the thumb. The Arden patent is a brace that uses rigid, yet flexible splints to prevent movement of a body part. On the other hand, the Grim patent is an adjustable splint that is not flexible. None of these designs include an element to heat or cool the body part that is immobilized.

A number of means of heating and cooling a body part have been developed. Examples are U.S. Pat. No. 6,840,955 by Ein and RE35113 by Grim. The patent by Ein is a therapeutic wrap that detects skin temperature and then heats or cools to a desired temperature. The Ein patent includes an electronic means of both heat and cooling the body and of detecting the changes of temperature. The Grim reissue is an orthopedic pad that can be heated or cooled. Neither invention immobilizes the body part that is being heated or cooled.

SUMMARY OF INVENTION

This invention is a cast for a body part that can both hold the body part stationary and change the temperature of the body part. The cast is constructed from a series of cells. Each cell is filled with a substance that can hold a certain temperature. The cast is mounted on a body part and then the substance in each cell changes the temperature of the body part.

The preferred embodiment of the invention envisions cells filled with a substance that can hold a cool temperature. The preferred substance is water that is either cold or frozen. Any substance can be used. A heated substance could be used as an alternative to a cooled substance. Possible substances include glycol and sodium carboxymethyl cellulose.

The cast holds the body part stationary by being secured around the body part. The cast has at least one set of fasteners that will secure the cast around the body part. Once the fastener is secured, the cast prevents significant movement by the body part. Different versions of the cast can be created that have a tighter or looser fit. Alternatively, the fastener can be adjustable so that different tightness of fit can be created.

The cast is secured to the body part by both the fastener and by a set of straps that help hold the cast in position. These straps extend from the cast to a body part that is near the first body part. The straps can also have at least one set of fasteners to hold the straps to the second body part. The preferred embodiment envisions a cast for a finger that is also secured by straps that attach to the wrist.

BRIEF DESCRIPTION OF THE DRAWINGS

The accompanying drawings, which are incorporated in and form part of the specification, illustrate the embodiments of the present invention and, together with the description, serve to explain the principles of the invention.

DETAILED DESCRIPTION OF THE DRAWINGS

Figure 1:
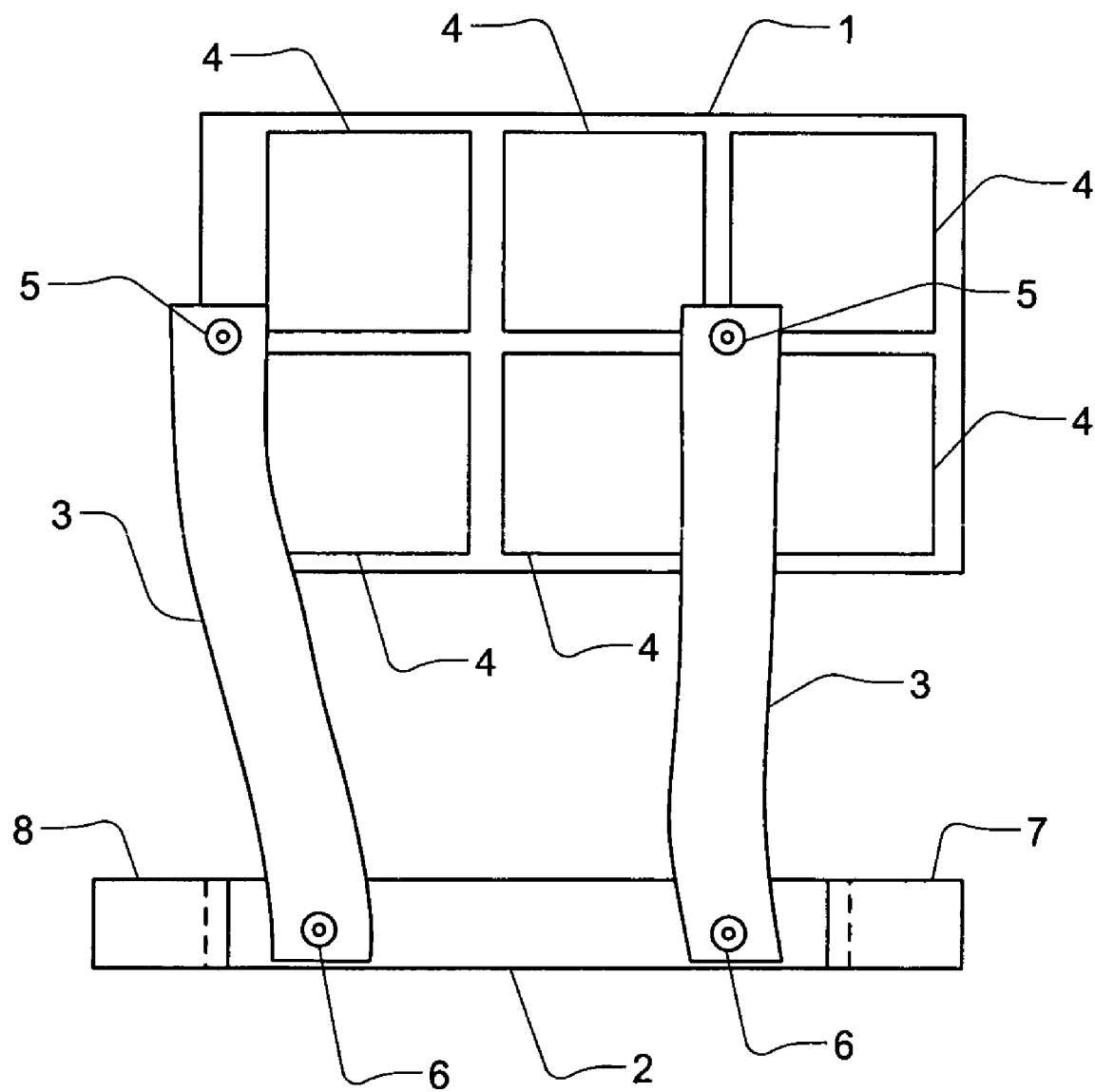
FIG. 1 is a picture of the cast.

FIG. 1 illustrates the cast. The cast 1 is attached to a wrist strap 2 by cast straps 3. The cast 1 is made of six cells 4. The cast straps 3 are attached to the cast 1 by cast fasteners 5. The cast fasteners 5 also are used to secure the cast 1 to a body part. The wrist strap 2 is attached to the cast straps 3 by wrist strap fasteners 6. The wrist strap 2 also has a reversible fastener 7 and its corresponding reversible fastener 8.

Figure 2:
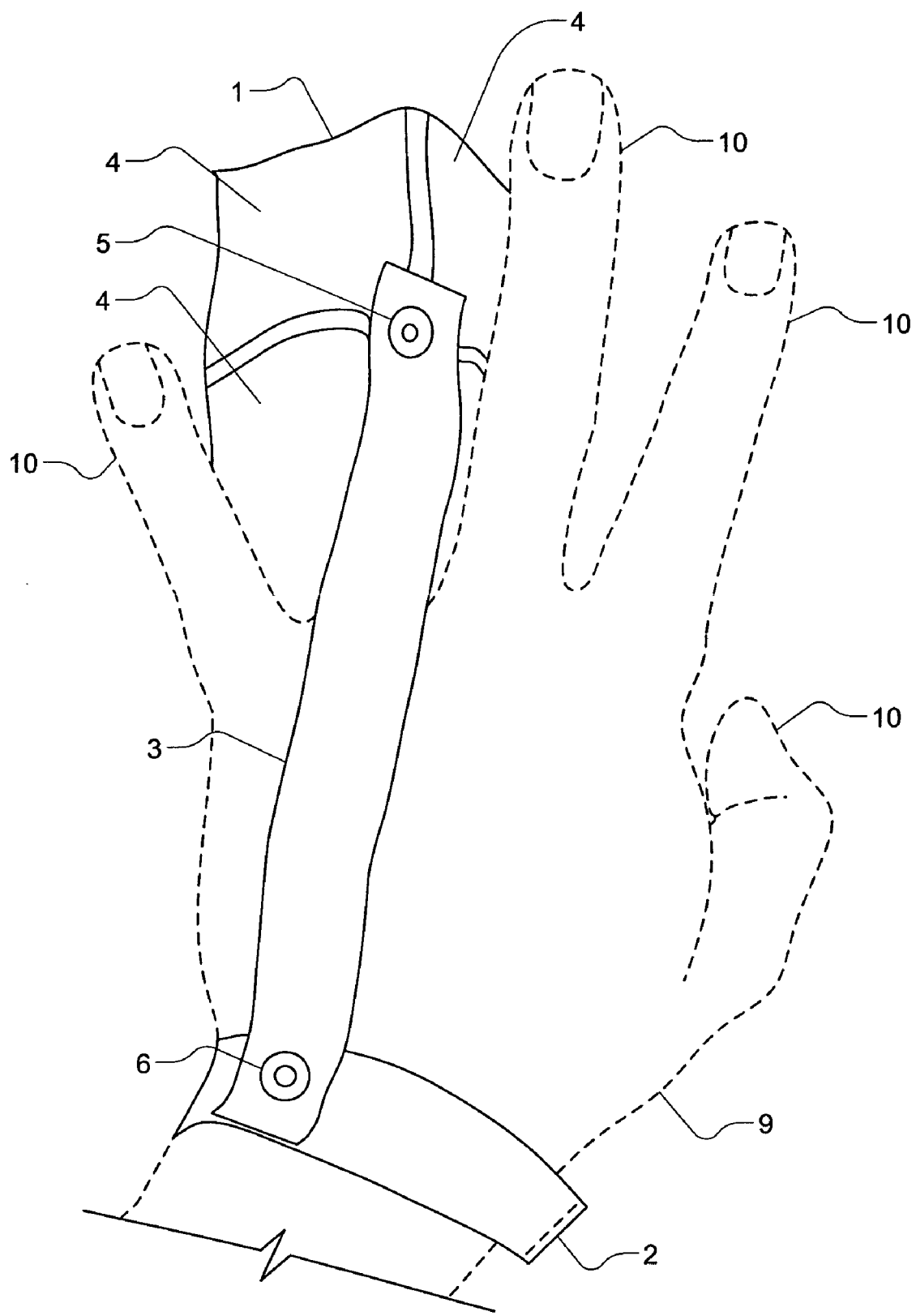
FIG. 2 is a picture of the cast in use on a finger.

FIG. 2 illustrates the cast in use on a finger. The cast 1 is attached to a wrist strap 2 by cast straps 3. The cast 1 is made of six cells 4. The cast straps 3 are attached to the cast 1 by cast fasteners 5. The cast fasteners 5 also are used to secure the cast 1 to a finger 10 on the hand 9. The cast fasteners 5 attach to each other, thus securing the cast 1 to the finger 10. The wrist strap 2 is attached to the cast straps 3 by wrist strap fasteners 6.

The cells 4 can be any size. The number of cells 4 in a cast 1 can be any number. The preferred embodiment envision six cells 4 that are of equal size. The cells 4 can be of different sizes from each other. The cast 1 can have spaces between the cells 4. These spaces can be of any size.

The cells 4 are filled with a filler that can hold a specific temperature. This temperature is determined by the heating or cooling of the filler in the cell 4. The filler is any substance that can retain a certain temperature or a certain range of temperature for a period of time and can radiate that temperature or range of temperature for a period of time. The preferred embodiment of the cell 4 contains a filler that is cooled so that the cast 1 cools the finger 10. A preferred embodiment envisions the substance to be water that is cooled or frozen inside the cell 4. Another preferred embodiment uses ice as the filler of cells 4. Other preferred embodiments envision a mixture or glycol, water and a polymer as the substance within each cell 4. Still other preferred embodiments envision a mixture of propylene glycol, water and sodium carboxymethyl cellulose as the substance in cells 4. Cells 4 could also contain only glycol, only water or only polymer. Cells 4 could also contain a combination of glycol and water, glycol and polymer, or water and polymer. In some versions of the invention, different cells 4 will have different fillers. In some versions of the invention, each cell 4 will have a different filler. In other versions of the invention, some cells 4 will have similar fillers while other cells 4 will have different fillers.

The cast fasteners 5 can be any type of fastener. Furthermore, any number of cast fasteners 5 can be used. The cast fasteners 5 can be adjustable so that when fastened the cast fasteners 5 tighten the cast 1 to a desired degree. The preferred embodiment envisions cast fasteners 5 that are snaps.

The invention envisions straps that hold the cast 1 to a body part near the body part that the cast 1 is attached. The preferred embodiment envisions the use of the cast 1 on a finger 10. In the preferred embodiment, the cast straps 3 attach the cast 1 to the wrist strap 2. The wrist strap 2 secures the cast 1 to the wrist of the hand 1 that has the finger 10. The cast 1 is on that finger 10. The wrist strap 2 has a reversible fastener 7 and a corresponding reversible fastener 8 that allow the wrist strap 2 to be put on and taken off the wrist of the hand 9. The reversible fastener 7 and the corresponding fastener 8 can be any kind of fastener. The preferred embodiment envisions a reversible fastener 7 and corresponding reversible fastener 8 that are snaps. Alternatively, The preferred embodiment envisions a reversible fastener 7 and corresponding reversible fastener 8 that is a fabric hook and loop fastener, such as VELCRO.

It should be noted that the cast 1 is described in a version for use with a finger. The cast 1 could be used with any body part by adjusting the size of the cast 1 and the length and configuration of the cast straps 3.

Although this invention has been illustrated by reference to specific embodiments, it will be apparent to those skilled in the art that various changes and modification may be made which clearly fall within the scope of the invention. The invention is intended to be protected broadly within the spirit and scope of the appended claims.

What is claimed is:

1. A cast assembly comprising:
   a flexible cast comprising a plurality of cells;
   a filler within each said cell, said filler being at a desired temperature;
   first, second and third straps, each defining first and second ends;
   first and second fasteners connected to said first strap for enabling said first strap to be attached to a first body part;
   third and fourth fasteners connecting said first ends of said second and said third straps, respectively, to said first strap;
   fifth and sixth fasteners connecting said second ends of said second and said third straps, respectively, to said cast; and
   said fifth and said sixth fasteners configured to be connected to each other when said cast is wrapped around and secured to a second body part near said first body part.

2. The cast assembly of claim 1 configured for use where said first body part is a wrist.

3. The cast assembly of claim 1 configured for use where the second body part is a finger.

4. The cast assembly of claim 1 where said filler is used to cool said second body part.

5. The cast assembly of claim 1 where said filler is water.

6. The cast assembly of claim 1 where said filler is ice.

7. The cast assembly of claim 1 where said filler is a mixture of glycol, water and a polymer.

8. The cast assembly of claim 1 where some of said cells do not contain the same filler as the other of said cells.

9. The cast assembly of claim 1 where the number of said cells in said cast is six.

10. The cast assembly of claim 1 where said first strap can be reversibly attached to said first body part.

11. The cast assembly of claim 1 where said fifth and said sixth fasteners are snaps.

12. The cast assembly of claim 1 where said first and said second fasteners are hook and loop fasteners.

13. The cast assembly of claim 1 where said first and said second fasteners are snaps.

\* \* \* \* \*